(12) United States Patent
Matheny et al.

(10) Patent No.: US 10,188,510 B2
(45) Date of Patent: Jan. 29, 2019

(54) PROSTHETIC TISSUE VALVES

(71) Applicant: CorMatrix Cardiovascular, Inc., Roswell, GA (US)

(72) Inventors: Robert G Matheny, Norcross, GA (US); Minh X Vo, Sugar Hill, GA (US); Carlos C Chang, Atlanta, GA (US); Selvamuthu K Natarajan, Alpharetta, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 103 days.

(21) Appl. No.: 15/206,833

(22) Filed: Jul. 11, 2016

(65) Prior Publication Data

US 2016/0317293 A1 Nov. 3, 2016

Related U.S. Application Data

(63) Continuation-in-part of application No. 14/960,354, filed on Dec. 5, 2015, now Pat. No. 9,907,649, and a continuation-in-part of application No. 14/229,854, filed on Mar. 29, 2014, now Pat. No. 9,308,084.

(51) Int. Cl.
*A61F 2/24* (2006.01)
*A61L 27/36* (2006.01)
*A61L 27/54* (2006.01)
*A61L 27/38* (2006.01)

(52) U.S. Cl.
CPC .......... *A61F 2/2412* (2013.01); *A61F 2/2409* (2013.01); *A61F 2/2457* (2013.01); *A61L 27/367* (2013.01); *A61L 27/3629* (2013.01); *A61L 27/3633* (2013.01); *A61L 27/3834* (2013.01); *A61L 27/3873* (2013.01); *A61L 27/54* (2013.01); *A61F 2230/0013* (2013.01); *A61F 2230/0067* (2013.01); *A61F 2250/0067* (2013.01); *A61L 2300/252* (2013.01); *A61L 2300/414* (2013.01); *A61L 2300/64* (2013.01); *A61L 2430/20* (2013.01)

(58) Field of Classification Search
CPC .... A61F 2/2412; A61F 2/2454; A61F 2/2457; A61F 2/2469; A61F 2/2475
See application file for complete search history.

(56) References Cited

U.S. PATENT DOCUMENTS

| | | |
|---|---|---|
| 3,417,777 A | 12/1968 | De Balsac et al. |
| 3,717,883 A | 2/1973 | Mosher |
| 5,413,599 A | 5/1995 | Imachi et al. |
| 6,440,164 B1 * | 8/2002 | DiMatteo ............. A61F 2/2412 623/1.24 |
| 6,705,585 B1 | 3/2004 | Roy |
| 6,790,237 B2 | 9/2004 | Stinson |
| 2001/0037808 A1 | 11/2001 | Deem et al. |
| 2006/0064174 A1 | 3/2006 | Zadno |
| 2007/0043431 A1 | 2/2007 | Melsheimer |
| 2007/0093887 A1 | 4/2007 | Case et al. |

(Continued)

*Primary Examiner* — Thomas J Sweet
*Assistant Examiner* — Megan Wolf
(74) *Attorney, Agent, or Firm* — Francis Law Group

(57) ABSTRACT

A prosthetic valve comprising a conical shaped sheet member comprising an extracellular matrix (ECM) composition, the sheet member having a plurality of ribbons projecting the sheet member proximal end, the distal ends of the ribbons being positioned proximate each other, wherein the sheet member comprises a conical shape.

9 Claims, 13 Drawing Sheets

(56) References Cited

U.S. PATENT DOCUMENTS

2008/0091261 A1* 4/2008 Long ................... A61F 2/2412
                                              623/1.24
2012/0303117 A1* 11/2012 Matheny ............ A61L 27/3633
                                              623/2.15
2014/0330369 A1* 11/2014 Matheny ............ A61F 2/2412
                                              623/2.14

* cited by examiner

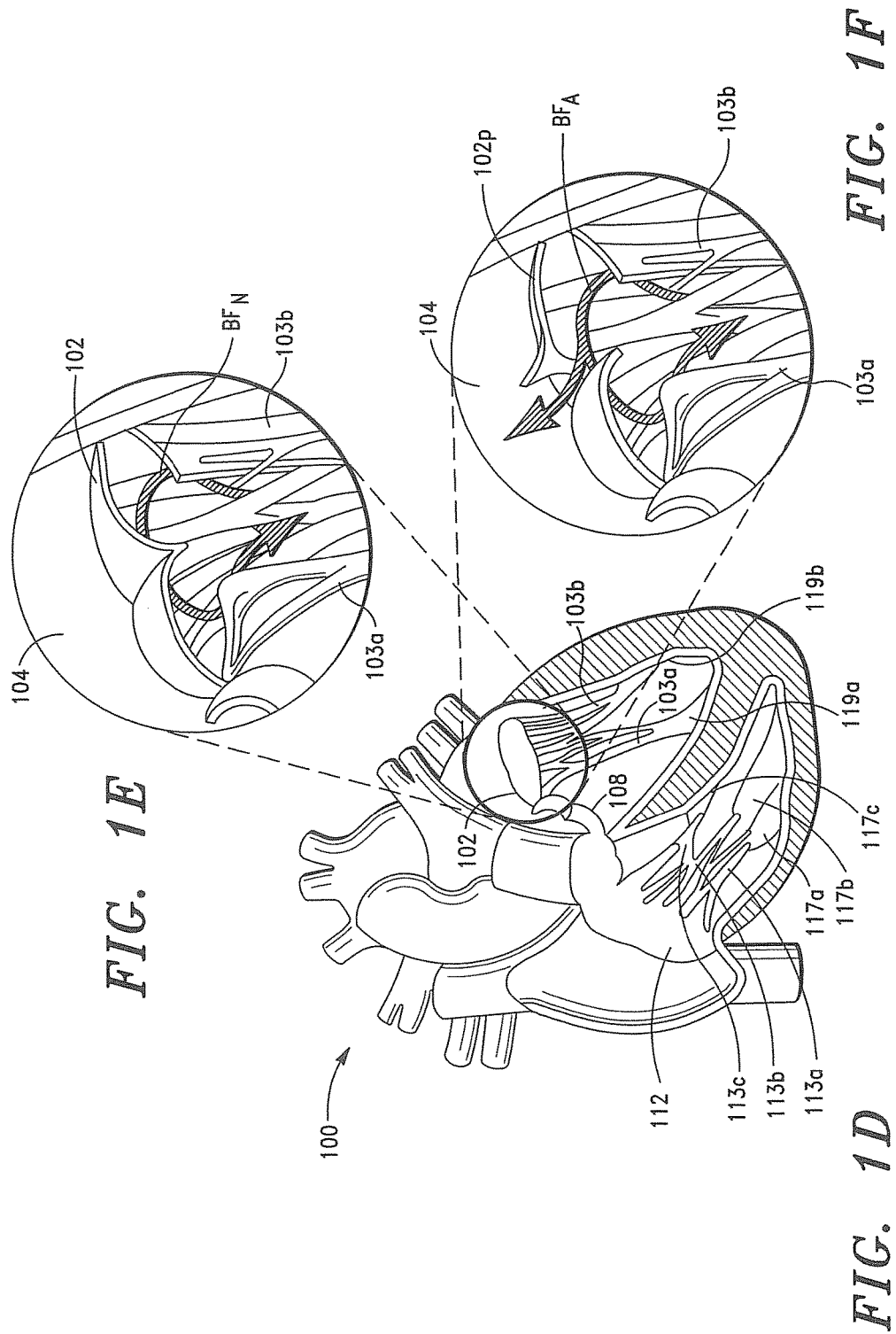

A-A

PROSTHETIC TISSUE VALVES

CROSS-REFERENCE TO RELATED APPLICATIONS

This application is a continuation-in-part application of U.S. application Ser. No. 14/960,354, filed on Dec. 5, 2015, now U.S. Pat. No. 9,907,649, which is a continuation-in-part application of U.S. application Ser. No. 14/229,854, filed on Mar. 29, 2014, now U.S. Pat. No. 9,308,084, which claims priority to U.S. Provisional Application No. 61/819,232, filed on May 3, 2013.

FIELD OF THE INVENTION

The present invention generally relates to prosthetic valves for replacing defective cardiovascular valves. More particularly, the present invention relates to prosthetic atrioventricular valves and methods for anchoring same to cardiovascular structures and/or tissue.

BACKGROUND OF THE INVENTION

As is well known in the art, the human heart has four valves that control blood flow circulating through the human body. Referring to FIGS. 1A and 1B, on the left side of the heart 100 is the mitral valve 102, located between the left atrium 104 and the left ventricle 106, and the aortic valve 108, located between the left ventricle 106 and the aorta 110. Both of these valves direct oxygenated blood from the lungs into the aorta 110 for distribution through the body.

The tricuspid valve 112, located between the right atrium 114 and the right ventricle 116, and the pulmonary valve 118, located between the right ventricle 116 and the pulmonary artery 120, however, are situated on the right side of the heart 100 and direct deoxygenated blood from the body to the lungs.

Referring now to FIGS. 1C and 1D, there are also generally five papillary muscles in the heart 100; three in the right ventricle 116 and two in the left ventricle 106. The anterior, posterior and septal papillary muscles 117a, 117b, 117c of the right ventricle 116 each attach via chordae tendinae 113a, 113b, 113c to the tricuspid valve 112. The anterior and posterior papillary muscles 119a, 119b of the left ventricle 106 attach via chordae tendinae 103a, 103b to the mitral valve 102 (see also FIG. 1E).

Since heart valves are passive structures that simply open and close in response to differential pressures, the issues that can develop with valves are typically classified into two categories: (i) stenosis, in which a valve does not open properly, and (ii) insufficiency (also called regurgitation), in which a valve does not close properly.

Stenosis and insufficiency can occur as a result of several abnormalities, including damage or severance of one or more chordeae or several disease states. Stenosis and insufficiency can also occur concomitantly in the same valve or in different valves.

Both of the noted valve abnormalities can adversely affect organ function and result in heart failure. By way of example, referring first to FIG. 1E, there is shown normal blood flow (denoted "$BF_N$") proximate the mitral valve 102 during closure. Referring now to FIG. 1F, there is shown abnormal blood flow (denoted "$BF_A$") or regurgitation caused by a prolapsed mitral valve 102p. As illustrated in FIG. 1F, the regurgitated blood "$BF_A$" flows back into the left atrium, which can, if severe, result in heart failure.

In addition to stenosis and insufficiency of a heart valve, surgical intervention may also be required for certain types of bacterial or fungal infections, wherein the valve may continue to function normally, but nevertheless harbors an overgrowth of bacteria (i.e. "vegetation") on the valve leaflets. The vegetation can, and in many instances will, flake off (i.e. "embolize") and lodge downstream in a vital artery.

If such vegetation is present on the valves of the left side (i.e., the systemic circulation side) of the heart, embolization can, and often will, result in sudden loss of the blood supply to the affected body organ and immediate malfunction of that organ. The organ most commonly affected by such embolization is the brain, in which case the patient can, and in many instances will, suffer a stroke.

Likewise, bacterial or fungal vegetation on the tricuspid valve can embolize to the lungs. The noted embolization can, and in many instances will, result in lung dysfunction.

Treatment of the noted heart valve dysfunctions typically comprises reparation of the diseased heart valve with preservation of the patient's own valve or replacement of the valve with a mechanical or bioprosthetic valve, i.e. a prosthetic valve.

Various prosthetic heart valves have thus been developed for replacement of natural diseased or defective heart valves. Illustrative are the tubular prosthetic tissue valves disclosed in Applicant's U.S. Pat. Nos. 9,044,319, 8,709,076 and 8,790,397, and Co-Pending U.S. application Ser. Nos. 13/560,573, 13/804,683, 13/480,347 and 13/480,324. A further tubular prosthetic valve is disclosed in U.S. Pat. Nos. 8,257,434 and 7,998,196.

Heart valve replacement requires a great deal of skill and concentration to achieve a secure and reliable attachment of a prosthetic valve to a cardiovascular structure or tissue. Various surgical methods for implanting a prosthetic valve have thus been developed.

The most common surgical method that is employed to implant a prosthetic valve (mitral or tricuspid) comprises suturing a circular synthetic ring of a prosthetic valve to the annular tissue of the heart where a diseased valve has been removed.

A major problem associated with prosthetic valves is tissue valves with gluteraldehyde cross-linked leaflets will calcify and deteriorate over time.

Another problem is mechanical valves will require anti-coagulation agents, such as Coumadin, which can cause side effects in high doses, such as uncontrolled bleeding.

Another problem is the valves do not remodel into normal tissue capable of regeneration and self repair.

Another problem is many valves must be placed with open heart surgery while the patient is on a heart-lung machine.

There is thus a need to provide improved prosthetic tissue valves and methods for attaching same to cardiovascular structures and/or tissue that maintain or enhance the structural integrity of the valve when subjected to cardiac cycle induced stress.

It is therefore an object of the present invention to provide improved prosthetic tissue valves and methods for implanting same that overcome the drawbacks and disadvantages associated with conventional prosthetic atrioventricular valves.

It is another object of the present invention to provide improved prosthetic tissue valves and methods for attaching same to cardiovascular structures and/or tissue that maintain or enhance the structural integrity of the valve when subjected to cardiac cycle induced stress.

It is another object of the present invention to provide improved prosthetic tissue valves and methods for attaching same to cardiovascular structures and/or tissue that preserve the structural integrity of the cardiovascular structure(s) when attached thereto.

It is another object of the present invention to provide improved methods for securely attaching prosthetic tissue valves to cardiovascular structures and/or tissue.

It is another object of the present invention to provide prosthetic tissue valves having means for secure, reliable, and consistently highly effective attachment to cardiovascular structures and/or tissue.

It is another object of the present invention to provide extracellular matrix (ECM) prosthetic tissue valves that induce host tissue proliferation, bioremodeling and regeneration of new tissue and tissue structures with site-specific structural and functional properties.

It is another object of the present invention to provide ECM prosthetic tissue valves that induce adaptive regeneration.

It is another object of the present invention to provide ECM prosthetic tissue valves that are capable of administering a pharmacological agent to host tissue and, thereby produce a desired biological and/or therapeutic effect.

SUMMARY OF THE INVENTION

The present invention is directed to prosthetic tissue valves that can be readily employed to selectively replace diseased or defective heart valves, and methods for attaching (or anchoring) same to cardiovascular structures and/or tissue.

In some embodiments of the invention, the prosthetic tissue valves comprise continuous tubular members.

In some embodiments of the invention, the prosthetic tissue valves comprise continuous conical shaped structural members.

In some embodiments of the invention, the proximal end of the prosthetic tissue valves comprise an annular ring that is designed and configured to securely engage the prosthetic tissue valves to a valve annulus and, hence, cardiovascular tissue associated therewith.

In some embodiments of the invention, the distal end of the prosthetic tissue valves having conical shaped structural members also comprise a structural ring.

According to the invention, the tubular member, conical shaped structural member, annular ring and structural ring can comprise various biocompatible materials.

In some embodiments of the invention, the tubular member and/or conical shaped structural member and/or annular ring and/or structural ring comprise an ECM composition comprising acellular ECM derived from a mammalian tissue source.

In a preferred embodiment of the invention, the mammalian tissue source is selected from the group comprising small intestine submucosa (SIS), urinary bladder submucosa (UBS), stomach submucosa (SS), central nervous system tissue, mesodermal tissue, i.e. mesothelial tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof.

In some embodiments of the invention, the ECM composition (and, hence, tubular member and/or conical shaped structural member and/or annular ring and/or structural ring formed therefrom) further comprises at least one additional biologically active agent or composition, i.e. an agent that induces or modulates a physiological or biological process, or cellular activity, e.g., induces proliferation, and/or growth and/or regeneration of tissue.

In some embodiments of the invention, the biologically active agent comprises a growth factor, including, without limitation, transforming growth factor alpha (TGF-α), transforming growth factor beta (TGF-β), fibroblast growth factor-2 (FGF-2), and vascular epithelial growth factor (VEGF).

In some embodiments of the invention, the ECM composition (and, hence, tubular member and/or conical shaped structural member and/or annular ring and/or structural ring formed therefrom) further comprises at least one pharmacological agent or composition (or drug), i.e. an agent or composition that is capable of producing a desired biological effect in vivo, e.g., stimulation or suppression of apoptosis, stimulation or suppression of an immune response, etc.

In some embodiments of the invention, the pharmacological agent comprises an anti-inflammatory agent.

In some embodiments of the invention, the pharmacological agent comprises a statin, i.e. a HMG-CoA reductase inhibitor.

In some embodiments of the invention, the annular ring and/or structural ring comprise a biocompatible polymeric material.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 1A-1D are schematic illustrations of a human heart;

FIG. 1E is an illustration of a normal mitral valve;

FIG. 1F is an illustration of a prolapsed mitral valve;

DETAILED DESCRIPTION OF THE PREFERRED EMBODIMENT

Figure 1A:
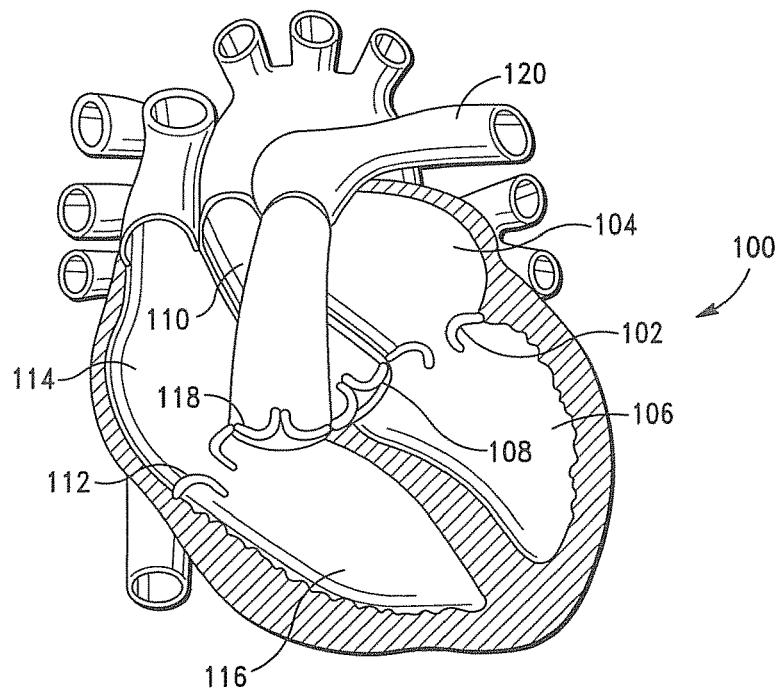
Figure 1B:
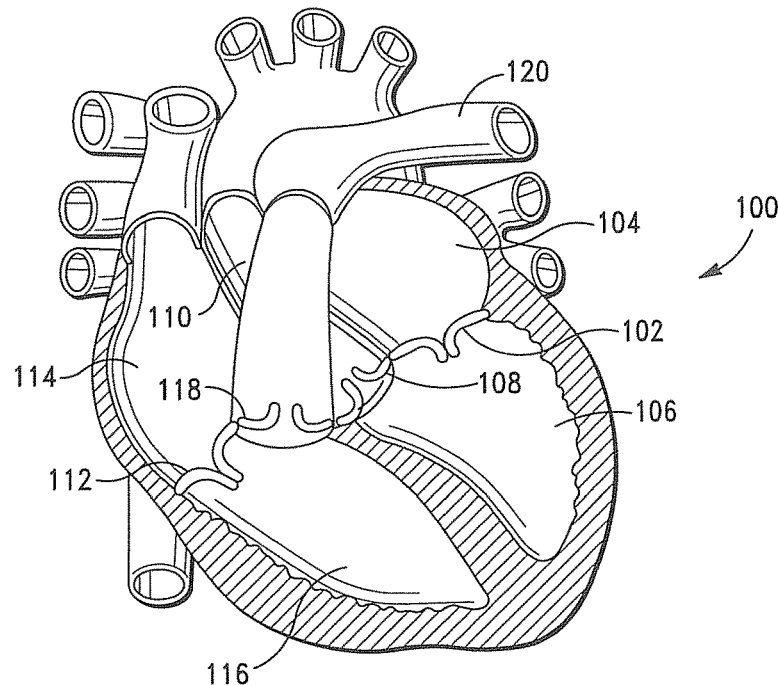
Figure 1C:
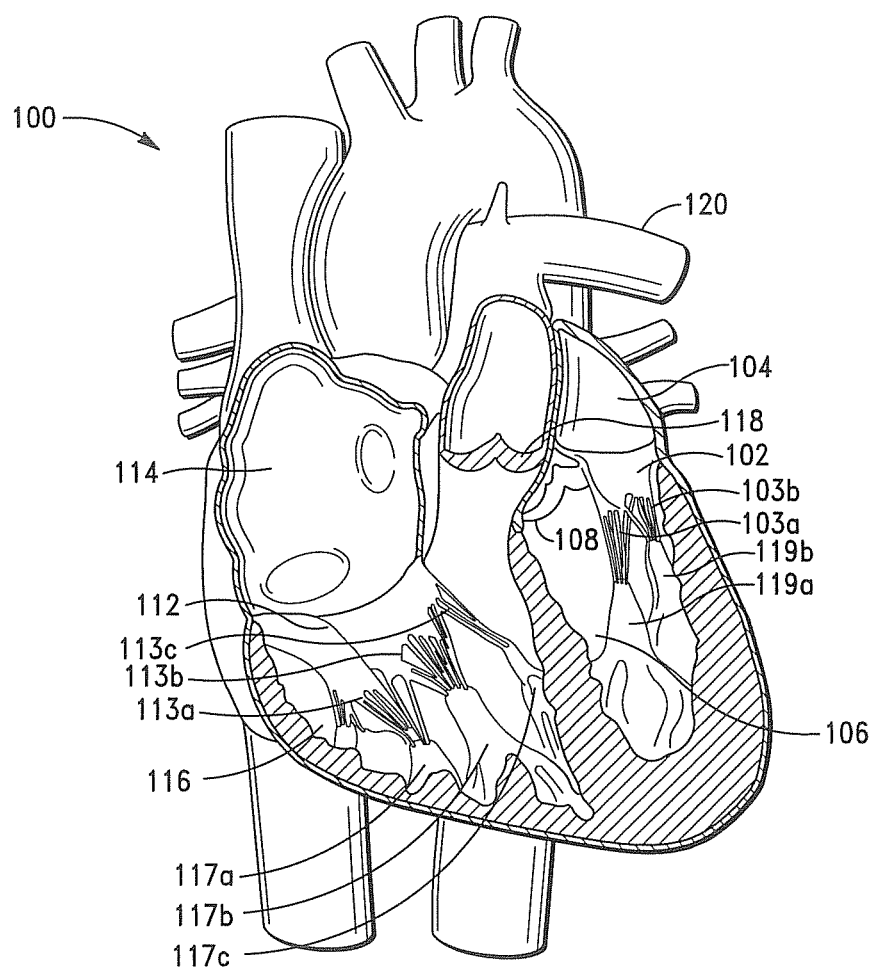

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "extracellular matrix", "ECM", and "ECM material" are used interchangeably herein, and mean and include a collagen-rich substance that is found in between cells in mammalian tissue, and any material processed therefrom, e.g. decellularized ECM. According to the invention, ECM can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The term "acellular ECM", as used herein, means and includes ECM that has a reduced content of cells, i.e. decellularized ECM.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

ECM can also be derived from basement membrane of mammalian tissue/organs, including, without limitation, urinary basement membrane (UBM), liver basement membrane (LBM), and amnion, chorion, allograft pericardium, allograft acellular dermis, amiotic membrane, Wharton's jelly, and combinations thereof.

Additional sources of mammalian basement membrane include, without limitation, spleen, lymph nodes, salivary glands, prostate, pancreas and other secreting glands.

According to the invention, the ECM can be derived from xenogeneic and allogeneic tissue sources.

ECM can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The term "biologically active agent", as used herein, means and includes agent that induces or modulates a physiological or biological process, or cellular activity, e.g., induces proliferation, and/or growth and/or regeneration of tissue.

The term "biologically active agent" thus means and includes, without limitation, the following growth factors: platelet derived growth factor (PDGF), epidermal growth factor (EGF), transforming growth factor alpha (TGF-α), transforming growth factor beta (TGF-β), fibroblast growth factor-2 (FGF-2), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

The term "biologically active agent" also means and includes, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogeneic cells, allogeneic cells, and post-natal stem cells.

The term "biologically active agent" also means and includes, without limitation, the following biologically active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, fibulin II, integrins, transmembrane molecules, thrombospondins, osteopontins, and angiotensin converting enzymes (ACE).

The term "biologically active composition", as used herein, means and includes a composition comprising a "biologically active agent".

The terms "pharmacological agent", "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent" and "drug" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPs), enzymes and enzyme inhibitors, anticoagulants and/or anti-thrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent" and "drug" also mean and include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent" and "drug" also mean and include the following Class I-Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent" and "drug" also mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent" and "drug" also mean and include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent" and "drug" also mean and include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent" and "drug" also mean and include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/ lignocaine, mepivacaine, prilocaine, ropivacaine, and trimecaine. Local anesthetics can further include combinations of the above from either amides or esters.

As indicated above, the terms "pharmacological agent", "active agent" and "drug" also mean and include an anti-inflammatory.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterol one, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The terms "pharmacological agent", "active agent" and "drug" also mean and include a statin, i.e. a HMG-CoA reductase inhibitor, including, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®).

The term "pharmacological composition", as used herein, means and includes a composition comprising a "pharmacological agent" and/or any additional agent or component identified herein.

The term "therapeutically effective", as used herein, means that the amount of the "pharmacological agent" and/or "biologically active agent" and/or "pharmacological composition" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to prosthetic tissue valves that can be readily employed to selectively replace diseased or defective valves in the heart, and methods for attaching (or anchoring) same to cardiovascular structures and/or tissue.

As discussed in detail below, in some embodiments of the invention, the prosthetic tissue valves comprise continuous tubular members.

As indicated above, in some embodiments of the invention, the proximal ends of prosthetic tissue valves of the invention comprise an annular ring that is designed and configured to securely engage the prosthetic tissue valves to a valve annulus (and, hence, cardiovascular tissue associated therewith).

In some embodiments of the invention, the annular ring comprises at least one anchoring mechanism that is configured to position the prosthetic tissue valves proximate a valve annulus, and maintain contact therewith for a predetermined anchor support time period. According to the invention, the anchoring mechanisms can comprise various forms and materials, such as disclosed in U.S. Pat. No. 9,044,319, which is incorporated by reference herein in its entirety.

In some embodiments of the invention, the anchoring mechanisms are configured to position ECM prosthetic tissue valves of the invention proximate a valve annulus, and maintain contact therewith for a predetermined temporary anchor support period of time within the process of tissue regeneration.

In some embodiments of the invention, the prosthetic valves comprise continuous conical shaped structural members.

In some embodiments, the conical shaped structural members and, hence, prosthetic tissue valves formed therefrom, similarly comprise an annular ring that is designed and configured to securely engage the conical shaped structural members and, hence, prosthetic tissue valves formed therefrom to a valve annulus and, hence, cardiovascular tissue associated therewith.

In some embodiments of the invention, the distal end of the conical shaped structural members and, hence, prosthetic tissue valves formed therefrom, comprises a structural ring.

According to the invention, the tubular members and conical shaped members can comprise various biocompatible materials and compositions formed therefrom.

In some embodiments of the invention, the tubular shaped member and conical shaped member comprise sheet members.

According to the invention, the tubular shaped sheet members and conical shaped sheet members can comprise single or multi-sheet members.

According to the invention, the sheet(s) can be formed into the tubular and conical shaped members of the invention and secured about the mating edges by various conventional means, e.g., suturing the mating edges together.

In some embodiments of the invention, the tubular shaped member and/or annular ring comprise an ECM composition comprising acellular ECM derived from a mammalian tissue source.

In some embodiments of the invention, the conical shaped structural member and/or annular ring and/or structural ring similarly comprise an ECM composition comprising acellular ECM derived from a mammalian tissue source.

As discussed in detail herein, it is contemplated that, following placement of a prosthetic tissue valve comprising an ECM composition, e.g., a conical shaped structural member comprising an ECM composition, (hereinafter "an ECM prosthetic tissue valve") on a cardiovascular structure (or structures) in a subject, e.g. valve annulus, and, hence, cardiovascular tissue associated therewith, the ECM prosthetic tissue valve will induce "modulated healing" of the cardiovascular structure(s) and tissue associated therewith.

As discussed in detail herein, it is contemplated that, following placement of an ECM prosthetic tissue valve on a cardiovascular structure (or structures) in a subject, the ECM prosthetic tissue valve will become populated with cells from the subject that will gradually remodel the ECM into cardiovascular tissue and tissue (and, hence, valve) structures.

It is further contemplated that, following placement of an ECM prosthetic tissue valve on a cardiovascular structure (or structures) in a subject, stem cells will migrate to the ECM prosthetic tissue valve from the point(s) at which the valve is attached to the cardiovascular structure, e.g., valve annulus, or structures, e.g., valve annulus and heart wall.

It is still further contemplated that the points at which an ECM prosthetic tissue valve is attached to a cardiovascular structure (or structures) in a subject will serve as points of constraint that direct the remodeling of the ECM into cardiovascular tissue and valve structures that are identical or substantially identical to properly functioning native cardiovascular tissue and valve structures.

It is still further contemplated that, during circulation of epithelial and endothelial progenitor cells after placement of an ECM prosthetic tissue valve on a cardiovascular structure (or structures), the surfaces of an ECM prosthetic tissue valve will rapidly become lined or covered with epithelial and/or endothelial progenitor cells.

As indicated above, in some embodiments of the invention, the proximal ends of prosthetic tissue valves of the invention comprise an annular ring that is designed and configured to securely engage the prosthetic tissue valves to a valve annulus (and, hence, cardiovascular tissue associated therewith).

As also indicated above, in some embodiments, the distal end of prosthetic tissue valves comprising a conical shaped structural member further comprise a structural ring.

According to the invention, the annular ring and structural ring can also comprise various biocompatible materials and compositions formed therefrom. Suitable biocompatible ring materials are disclosed in Co-Pending U.S. application Ser. No. 14/953,548, which is incorporated by reference herein.

In some embodiments of the invention, the annular ring and/or structural ring comprise a polymeric composition comprising a biodegradable polymeric material. According to the invention, suitable biodegradable polymeric materials comprise, without limitation, polycaprolactone (PCL), Artelon® (porous polyurethaneurea), polyglycolide (PGA), polylactide (PLA), poly(ε-caprolactone) (PCL), poly dioxanone (a polyether-ester), poly lactide-co-glycolide, polyamide esters, polyalkalene esters, polyvinyl esters, polyvinyl alcohol, and polyanhydrides.

According to the invention, the polymeric composition can further comprise a natural polymer, including, without limitation, polysaccharides (e.g. starch and cellulose), proteins (e.g., gelatin, casein, silk, wool, etc.), and polyesters (e.g., polyhydroxyalkanoates).

The polymeric composition can also comprise a hydrogel composition, including, without limitation, polyurethane, poly(ethylene glycol), poly(propylene glycol), poly(vinylpyrrolidone), xanthan, methyl cellulose, carboxymethyl cellulose, alginate, hyaluronan, poly(acrylic acid), polyvinyl alcohol, acrylic acid, hydroxypropyl methyl cellulose, methacrylic acid, αβ-glycerophosphate, κ-carrageenan, 2-acrylamido-2-methylpropanesulfonic acid, and β-hairpin peptide.

According to the invention, the polymeric composition can further comprise a non-biodegradable polymer, including, without limitation, polytetrafluoro ethylene (Teflon®) and polyethylene terephthalate (Dacron®).

In some embodiments of the invention, the polymeric composition comprises poly(urethane urea); preferably, Artelon® distributed by Artimplant AB in Goteborg, Sweden.

In some embodiments, the polymeric composition comprises poly(glycerol sebacate) (PGS).

In some embodiments of the invention, annular ring and/or structural ring and, hence, prosthetic valves formed therefrom comprise a biocompatible metal. According to the invention, suitable metals comprise, without limitation, Nitinol®, stainless steel and magnesium.

In a preferred embodiment of the invention, the tubular shaped members comprise an ECM composition comprising acellular ECM derived from a mammalian tissue source.

In a preferred embodiment, the conical shaped structural member similarly comprises an ECM composition comprising acellular ECM derived from a mammalian tissue source.

In some embodiments, the annular ring and/or structural ring also comprise an ECM composition comprising acellular ECM derived from a mammalian tissue source.

According to the invention, the ECM can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety.

The mammalian tissue sources include, without limitation, the small intestine, large intestine, stomach, lung, liver, kidney, pancreas, peritoneum, placenta, heart, bladder, prostate, tissue surrounding growing enamel, tissue surrounding growing bone, and any fetal tissue from any mammalian organ.

The mammalian tissue can thus comprise, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof. The ECM can also comprise collagen from mammalian sources.

In some embodiments of the invention, the mammalian tissue source comprises mesothelial tissue.

In some embodiments, the mammalian tissue source comprises an adolescent mammalian tissue source, e.g. tissue derived from a porcine mammal less than 3 years of age.

According to the invention, the ECM can also be derived from the same or different mammalian tissue sources, as disclosed in Co-Pending application Ser. Nos. 13/033,053 and 13/033,102; which are incorporated by reference herein.

In a preferred embodiment of the invention, the ECM comprises sterilized and decellularized (or acellular) ECM.

According to the invention, the ECM can be sterilized and decellularized by various conventional means.

In some embodiments of the invention, the ECM is sterilized and decellularized via applicant's proprietary process disclosed in Co-Pending U.S. application Ser. No. 13/480,205; which is expressly incorporated by reference herein in its entirety.

In some embodiments of the invention, the ECM comprises crosslinked ECM. According to the invention, the ECM can be crosslinked by various conventional materials and methods.

As stated above, in some embodiments of the invention, the ECM composition (and, hence, tubular shaped member and/or conical shaped structural member and/or annular ring and/or structural ring formed therefrom) further comprises at least one additional biologically active agent or composition, i.e. an agent that induces or modulates a physiological or biological process, or cellular activity, e.g., induces proliferation, and/or growth and/or regeneration of tissue.

According to the invention, suitable biologically active agents include any of the aforementioned biologically active agents, including, without limitation, the aforementioned growth factors, cells and proteins.

In some embodiments of the invention, the ECM composition (and, hence, tubular shaped member and/or conical shaped structural member and/or annular ring and/or structural ring formed therefrom) further comprises at least one pharmacological agent or composition (or drug), i.e. an agent or composition that is capable of producing a desired biological effect in vivo, e.g., stimulation or suppression of apoptosis, stimulation or suppression of an immune response, etc.

According to the invention, suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises an anti-inflammatory agent.

In some embodiments, the pharmacological agent comprises a statin, i.e. a HMG-CoA reductase inhibitor. According to an aspect of the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

It has been found that the noted statins exhibit numerous beneficial properties that provide several beneficial biochemical actions or activities in vivo; particularly, when the statins are a component of an ECM composition comprising acellular ECM, i.e. a statin augmented ECM composition. The properties and beneficial actions are set forth in Applicant's U.S. Pat. No. 9,072,816 and Co-Pending application Ser. No. 13/782,024, filed on Mar. 1, 2013 and Ser. No. 14/554,730, filed on Nov. 26, 2014; which are incorporated by reference herein in their entirety.

In some embodiments of the invention, the pharmacological agent comprises chitosan. As also set forth in detail in U.S. Pat. No. 9,072,816, chitosan similarly exhibits numerous beneficial properties that provide several beneficial biochemical actions or activities in vivo; particularly when chitosan is a component of an ECM composition comprising acellular ECM.

As indicated above, it is contemplated that, following placement of an ECM prosthetic tissue valve, i.e. a prosthetic tissue valve comprising an ECM composition, on a cardiovascular structure (or structures) in a subject, e.g. valve annulus, and, hence, cardiovascular tissue associated therewith, the ECM prosthetic tissue valve will induce "modulated healing" of the cardiovascular structure(s) and cardiovascular tissue associated therewith.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments of the invention, the ECM prosthetic tissue valves of the invention are specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments, "modulated healing" means and includes the ability of an ECM prosthetic tissue valve of the invention to restrict the expression of inflammatory components. By way of example, according to the invention, when a tubular member or conical shaped member (and/or annular ring and/or structural ring) of a prosthetic tissue valve comprises a statin augmented ECM composition, i.e. a composition comprising ECM and a statin, and the ECM prosthetic tissue valve is positioned proximate damaged biological tissue, e.g., attached to a valve annulus, the ECM prosthetic tissue valve restricts expression of monocyte chemoattractant protein-1 (MCP-1) and chemokine (C-C) motif ligand 2 (CCR2).

In some embodiments of the invention, "modulated healing" means and includes the ability of an ECM prosthetic tissue valve of the invention to alter a substantial inflammatory phase (e.g., platelet or fibrin deposition) at the beginning of the tissue healing process. As used herein, the phrase "alter a substantial inflammatory phase" refers to the ability of a prosthetic tissue valve of the invention to substantially reduce the inflammatory response at a damaged tissue site, e.g. valve annulus, when in contact with tissue at the site.

In such an instance, a minor amount of inflammation may ensue in response to tissue injury, but this level of inflammation response, e.g., platelet and/or fibrin deposition, is substantially reduced when compared to inflammation that takes place in the absence of an ECM prosthetic tissue valve of the invention.

The term "modulated healing" also refers to the ability of an ECM prosthetic tissue valve of the invention to induce host tissue proliferation, bioremodeling, including neovascularization, e.g., vasculogenesis, angiogenesis, and intussusception, and regeneration of tissue structures with site-specific structural and functional properties, when disposed proximate damaged tissue, e.g. valve annulus.

Thus, in some embodiments of the invention, the term "modulated healing" means and includes the ability of an ECM prosthetic tissue valve of the invention to modulate inflammation and induce host tissue proliferation and remodeling, when disposed proximate damaged tissue.

It is further contemplated that, during a cardiac cycle after placement of an ECM prosthetic tissue valve on a valve structure or structures, wherein the ECM prosthetic tissue valve is subjected to physical stimuli, adaptive regeneration of the prosthetic tissue valve is also induced.

By the term "adaptive regeneration," it is meant to mean the process of inducing modulated healing of damaged tissue concomitantly with stress-induced hypertrophy of an ECM prosthetic tissue valve of the invention, wherein the ECM prosthetic tissue valve adaptively remodels and forms functioning valve structures that are substantially identical to native valve structures.

As indicated above, it is further contemplated that the points at which an ECM prosthetic tissue valve is attached to a cardiovascular structure (or structures) in a subject will serve as points of constraint that direct the remodeling of the ECM into cardiovascular tissue and valve structures that are substantially identical to properly functioning native cardiovascular tissue and valve structures.

Referring now to FIGS. 2-5, two (2) embodiments of a prosthetic tissue valve of the invention will be described in detail.

Figure 2:
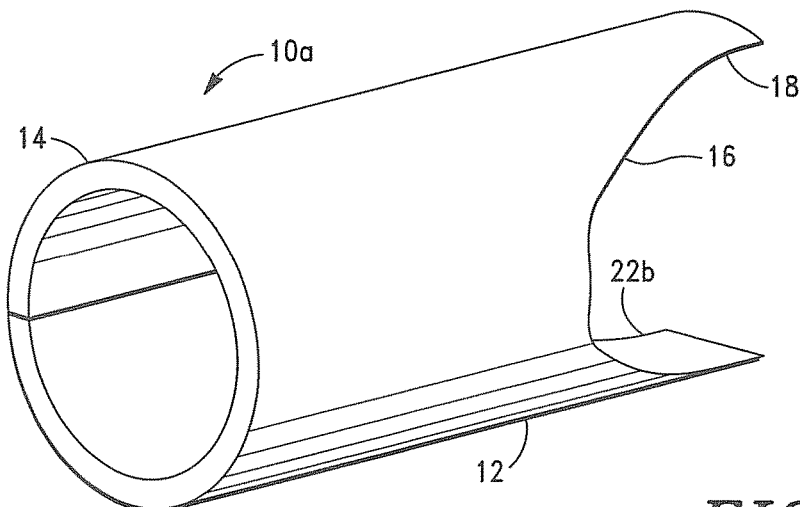
FIG. 2 is a perspective view of one embodiment of a prosthetic tissue valve, in accordance with the invention.
Figure 3:
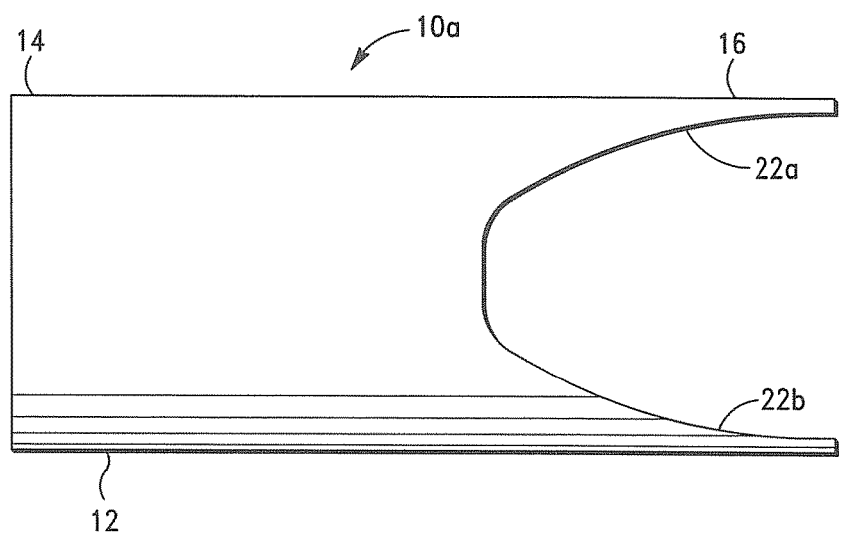
FIG. 3 is a side plane view of the prosthetic tissue valve shown in FIG. 2, in accordance with the invention.

Referring first to FIGS. 2 and 3, in one embodiment of the invention, the prosthetic tissue valve 10a comprises a continuous tubular member 12 having first or "proximal" and second or "distal" ends 14, 16. In some embodiments of the invention, the valve 10a further comprises at least one internal leaflet, such as disclosed in U.S. Pat. No. 8,709,076 and Co-Pending U.S. application Ser. No. 13/804,683, which are incorporated by reference herein.

In some embodiments, the tubular member 12 comprises a leaflet forming interior surface, such as disclosed in Co-Pending U.S. application Ser. Nos. 13/480,324 and 13/480,347, which are similarly incorporated by reference herein.

According to the invention, the tubular member 12 can comprise various biocompatible materials, including, without limitation, mammalian tissue, e.g., bovine tissue.

In some embodiments of the invention, the tubular member 12 comprises a biocompatible polymeric material. According to the invention, suitable polymeric materials comprise Dacron®, polyether ether ketone (PEEK), and like materials.

As indicated above, in some embodiments, the tubular member 12 comprises an ECM composition comprising ECM from a mammalian tissue source. According to the invention, the ECM can be derived from various mammalian tissue sources including, without limitation, small intestine submucosa (SIS), urinary bladder submucosa (UBS), stomach submucosa (SS), central nervous system tissue, mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof.

According to the invention, the ECM can also comprise collagen from mammalian sources.

As also indicated above, the ECM preferably comprises acellular ECM.

In some embodiments of the invention, the ECM composition and, hence, tubular member 12 formed therefrom, further comprises at least one additional biologically active agent or composition, i.e. an agent that induces or modulates a physiological or biological process, or cellular activity, e.g., induces proliferation, and/or growth and/or regeneration of tissue.

According to the invention, suitable biologically active agents include any of the aforementioned biologically active agents.

In some embodiments of the invention, the ECM composition and, hence, tubular member 12 formed therefrom, further comprises at least one pharmacological agent or composition (or drug), i.e. an agent or composition that is capable of producing a desired biological effect in vivo, e.g., stimulation or suppression of apoptosis, stimulation or suppression of an immune response, etc.

According to the invention, suitable pharmacological agents and compositions include any of the aforementioned agents, including, without limitation, antibiotics and anti-inflammatories.

In a preferred embodiment of the invention, the distal end 16 of the tubular member 12 includes cardiovascular structure engagement means 18 that is designed and configured to securely engage the member 12 and, hence, prosthetic tissue valve 10a formed therefrom, to cardiovascular structures, such as selective papillary muscles and/or cardiovascular tissue.

As illustrated in FIGS. 2 and 3, in some embodiments of the invention, the cardiovascular structure engagement means 18 comprises a pair of valve leaflet extensions 22a, 22b, which, in some embodiments of the invention, extend from a valve leaflet to mimic the chordae tendineae. According to the invention, the valve leaflet extensions 22a, 22b can be disposed at various positions about the periphery of the distal end 16 of the tubular member 12.

In some embodiments of the invention, wherein the prosthetic tissue valve 10a is employed to replace a mitral valve, the leaflet extensions 22a, 22b are preferably spaced at approximately 0° and 120° about the periphery of the distal end 16 of the tubular member 12.

According to the invention, the valve leaflet extensions 22a, 22b can also have various predetermined lengths to accommodate attachment to desired cardiovascular structures, e.g., selective papillary muscles.

The valve leaflet extensions 22a, 22b can also comprise the same material as the tubular member 12 or a different material, e.g. tubular member 12 comprises SIS and the valve leaflet extensions 22a, 22b comprise a polymeric material.

Figure 4:
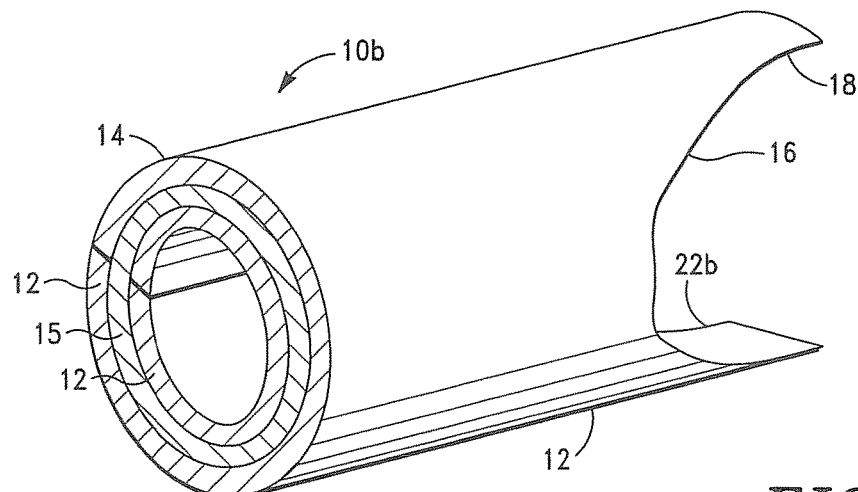
FIG. 4 is a perspective partial sectional view of another embodiment of a prosthetic tissue valve shown in FIG. 2 having an annular ring disposed at the proximal end of the valve, in accordance with the invention.
Figure 5:
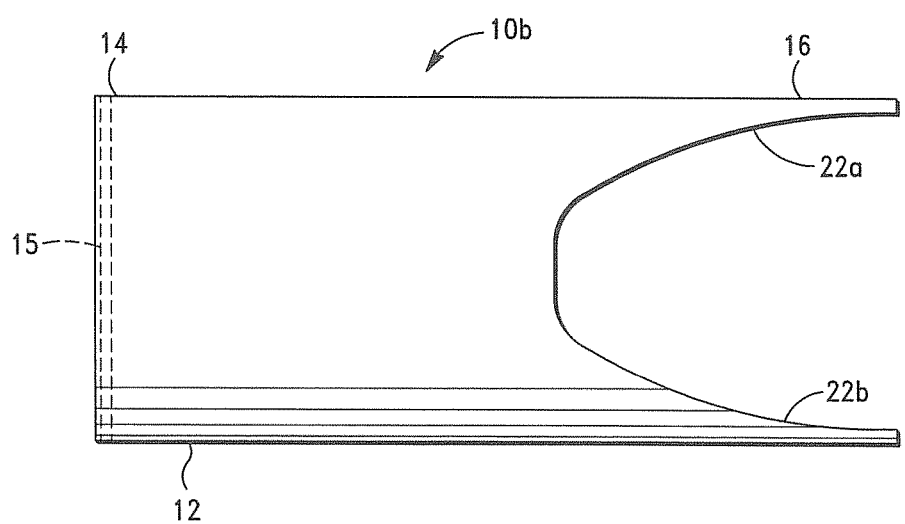
FIG. 5 is a side plane view of the prosthetic tissue valve shown in FIG. 4, in accordance with the invention.

Referring now to FIGS. 4 and, 5, in a further embodiment of the invention, the prosthetic tissue valve 10a shown in FIGS. 2 and 3 further comprises an annular ring 15 that is disposed on the proximal end 14 of the valve 10a, forming valve 10b. As indicated above, suitable annular rings and ring materials are disclosed in Co-Pending U.S. application Ser. No. 14/953,548.

Figure 6:
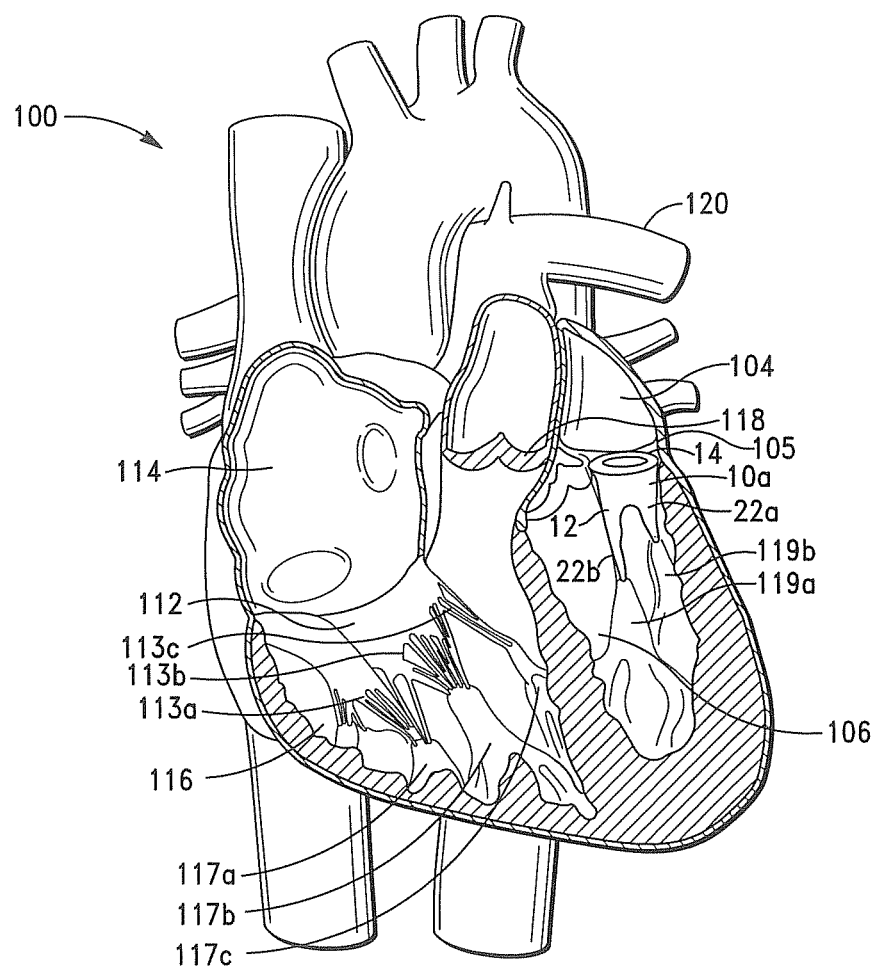
FIG. 6 is an illustration of the prosthetic tissue valve shown in FIG. 4 secured to the mitral valve annulus region and papillary muscles, in accordance with the invention.

Referring now to FIG. 6, placement of prosthetic tissue valve 10a proximate a mitral valve region will be described in detail.

According to the invention, the valve 10a is disposed proximate the mitral valve region. The initial placement of the valve 10a can be achieved by various conventional means, including limited access heart surgery and percutaneous delivery.

The proximal end 14 of the valve 12 is then sutured to the valve annulus 105. The valve leaflet extensions 22a, 22b are then attached directly to the papillary muscles 119a, 119b.

It is contemplated that, following attachment of the valve leaflet extensions 22a, 22b to the papillary muscles 119a, 119b, the valve leaflet extensions 22a, 22b fuse to the papillary muscles 119a, 119b and, in some embodiments, the valve leaflet extensions 22a, 22b remodel and regenerate functioning native chordae tendineae.

As indicated above, when the prosthetic tissue valve 10a (and valve 10b) comprises an ECM prosthetic tissue valve, it is also contemplated that the points at which the valve leaflet extensions 22a, 22b connect to the papillary muscles 119a, 119b and the proximal end 14 of the valve 12 is attached to the valve annulus 105 will serve as points of constraint that direct the remodeling of the prosthetic tissue valve 10a (and valve 10b) into valve tissue and/or valve structures, including chordae tendineae, that are identical or substantially identical to properly functioning native valve tissue and valve structures.

According to the invention, the valve leaflet extensions 22a, 22b and noted placement and attachment thereof significantly enhances the strength and, hence, structural integrity of the prosthetic tissue valves 10a, 10b shown in FIGS. 2-5. The valve leaflet extensions 22a, 22b and noted placement and attachment thereof also preserves the structural integrity of the papillary muscles 119a, 119b.

The valve leaflet extensions 22a, 22b (and noted placement and attachment thereof) thus significantly reduces the risk of suture failure and rupture of the prosthetic valve tissue proximate the papillary muscles 119a, 119b. The valve leaflet extensions 22a, 22b and noted placement and attachment thereof) also significantly reduce the risk of rupture of the papillary muscles 119a, 119b.

Figure 7A:
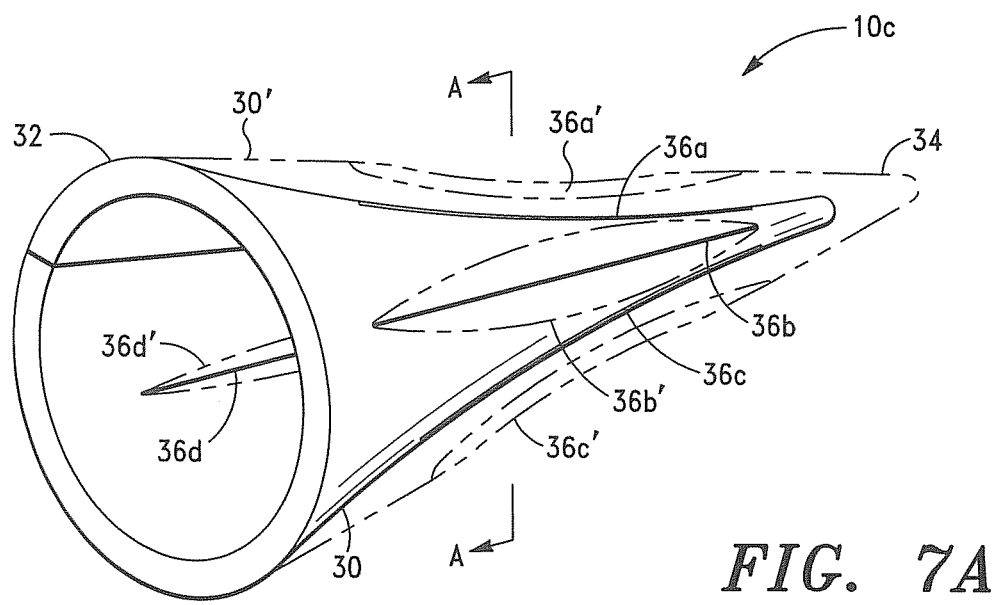
FIG. 7A is a perspective view of another embodiment of a prosthetic tissue valve, in accordance with the invention.
Figure 7B:
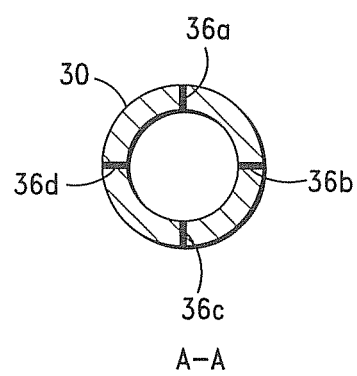
FIG. 7B is an end plane view of the prosthetic tissue valve shown in FIG. 7A, in accordance with the invention.

Referring now to FIGS. 7A and 7B, there is shown another embodiment of a prosthetic tissue valve of the invention (denoted "10c"). As illustrated in FIG. 7A, the prosthetic tissue valve 10c comprises a continuous, single sheet conical shaped member 30.

In a preferred embodiment, the conical shaped member 30 similarly comprises an ECM composition comprising acellular ECM derived from one of the aforementioned mammalian tissue sources, including, without limitation, small intestine submucosa (SIS), urinary bladder submucosa (UBS), mesothelial tissue, placental tissue and cardiac tissue.

As illustrated in FIG. 7A, the prosthetic tissue valve 10c further comprises proximal and distal ends 32, 34. According to the invention, the proximal end 32 of the valve 10c is sized and configured to engage a valve annulus region of a mammalian heart.

Figure 9:
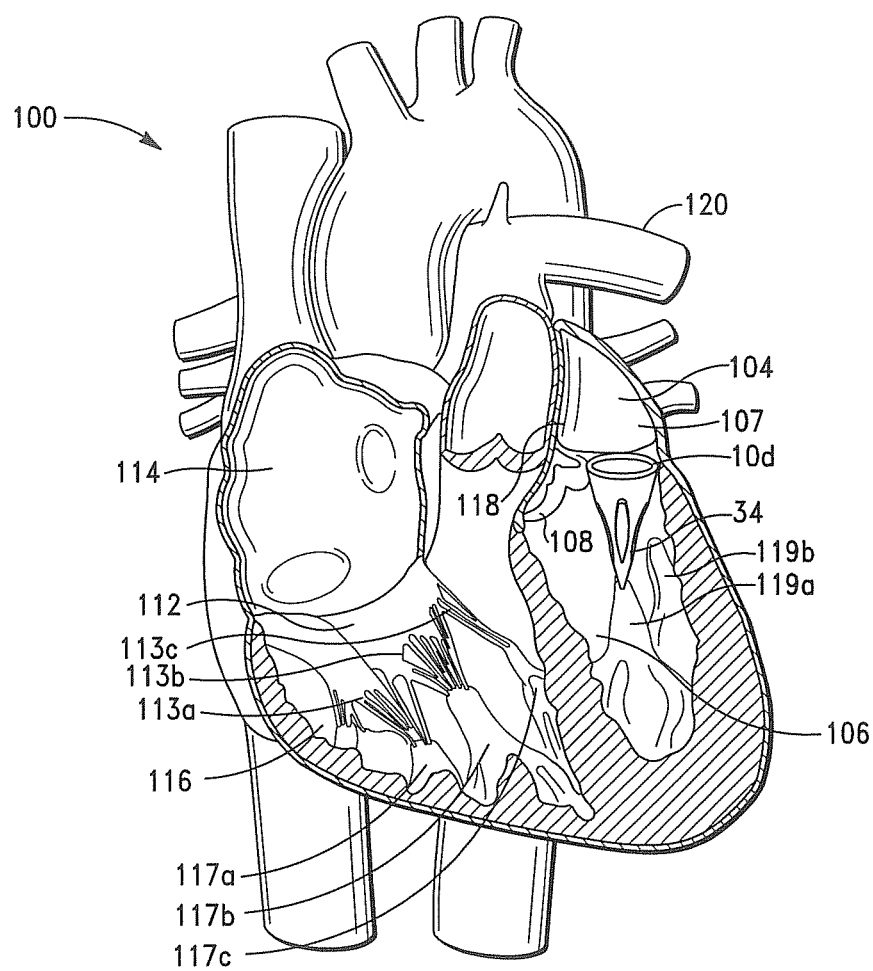
FIG. 9 is an illustration of the prosthetic tissue valve shown in FIG. 7C secured to the mitral valve annulus region, in accordance with the invention.

As further illustrated in FIG. 7A, the distal end 34 of the valve 10c is closed and, thus, is configured to block fluid flow therethrough when the proximal end 32 of the valve 10c is engaged to a cardiovascular structure, such as shown in FIG. 9, and the interstices 36a-36d (discussed below) are in closed position and opened positions.

In some embodiments of the invention, the proximal end 32 of the valve 10c (and valves 10d and 10e, discussed below) has an outer diameter in the range of approximately 1.0 mm to 5 cm.

According to the invention, the conical shaped member 30 and, hence, prosthetic tissue valve 10c can (and valves 10d-10e) comprise any length. In some embodiments of the invention, prosthetic tissue valve 10c (and valves 10d-10e) has a length in the range of approximately 5 mm to 150 mm.

In some embodiments of the invention, the conical shaped member 30 and, hence, prosthetic tissue valve 10c (and valves 10d-10e) has a proximal end diameter and length ratio in the range of 5:1 to 2:1.

As illustrated in FIGS. 7A and 7B, the prosthetic tissue valve 10c further comprises a plurality of open regions (referred to hereinafter as "interstices") 36a-36d that are preferably disposed linearly over a portion of the length of the member 30 between the proximal and distal ends 32, 34.

In a preferred embodiment of the invention, the conical shaped member 30 and, hence, prosthetic tissue valve 10c, is configured to transition from an expanded position, as shown in phantom and denoted 30' in FIG. 7A, when the proximal end 32 of conical shaped member 30 is engaged to a cardiovascular structure and receives fluid flow therein that exhibits a positive flow pressure, to a collapsed position, as denoted 30 in FIG. 7A, when the fluid flow exhibits a negative flow pressure.

In a preferred embodiment, the interstices 36a-36d are configured to transition from an open position (denoted 36a', 36b', 36c' and 36d') when the conical shaped member 30 is in the expanded position denoted 30' in FIG. 7A, to a closed position (denoted 36a, 36b, 36c and 36d) when the conical shaped member 30 is in the collapsed position denoted 30 in FIG. 7A.

As indicated above, the closed distal end 34 of the conical shaped member 30 is configured to block fluid flow therethrough when the plurality of linear interstices 36a-36d are in the open and closed positions, whereby, when the proximal end 32 of the conical shaped member 30 is engaged to a cardiovascular structure, fluid flow exhibiting a positive flow pressure is introduced into the conical shaped member 30 and the conical shaped member 30 is in an expanded position, and the plurality of linear interstices 36a-36d are in the open position (denoted 36a', 36b', 36c' and 36d'), the plurality of linear interstices 36a-36d allow the fluid flow to be transmitted through the plurality of open linear interstices 36a', 36b', 36c' and 36d' and, hence, conical shaped member 30, and when the fluid flow exhibits a negative flow pressure and the conical shaped member 30 is in the collapsed position, and the plurality of linear interstices 36a-36d are in the closed position (denoted 36a, 36b, 36c and 36d), the plurality of closed linear interstices 36a, 36b, 36c and 36d and the closed distal end 34 of the conical shaped member 30 block fluid flow through the member 30.

In some embodiments of the invention, the linear interstices 36a-36d have a length that is in the range of approximately 10% to 98% of the overall length of the conical shaped member 30.

In some embodiments, the width of the linear interstices 36a-36d is in the range of approximately 1 mm to 30 mm.

According to the invention, the linear interstices 36a-36d can have the same length and width or different lengths and widths. In some embodiments of the invention, the linear interstices 36a-36d have the same length and width.

In some embodiments of the invention, the linear interstices 36a-36d have a length that is in the range of approximately 10% to 98% of the overall length of the conical shaped member 30.

In some embodiments, the width of the linear interstices 36a-36d is in the range of approximately 1 mm to 30 mm.

According to the invention, the linear interstices 36a-36d can have the same length and width or different lengths and widths. In some embodiments of the invention, the linear interstices 36a-36d have the same length and width.

Figure 7C:
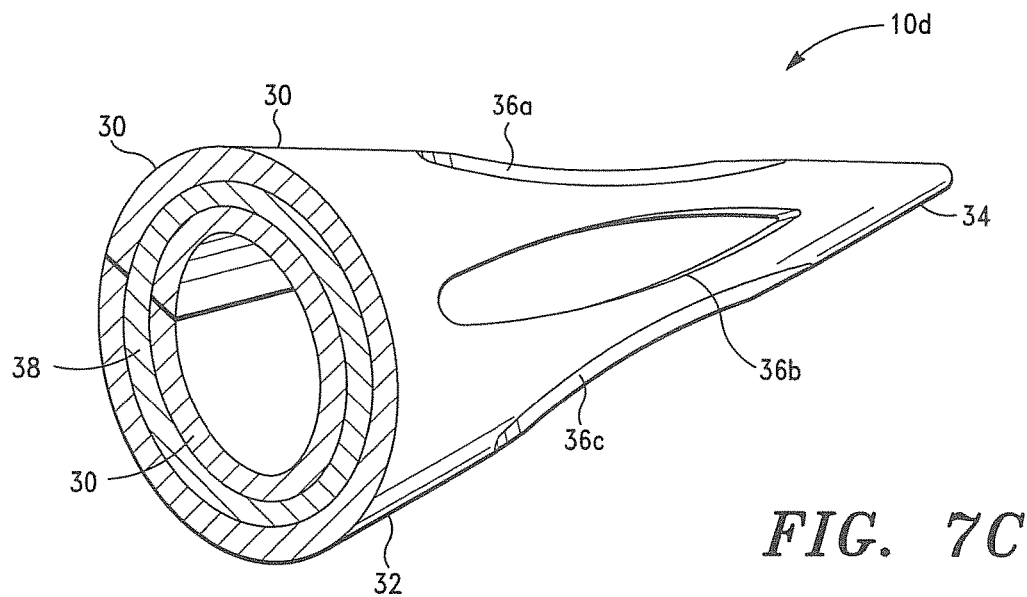
FIG. 7C is a perspective view partial sectional of another embodiment of a prosthetic tissue valve shown in FIG. 7A having an annular ring disposed at the proximal end of the valve, in accordance with the invention.

Referring now to FIG. 7C, there is shown another embodiment of the prosthetic tissue valve 10c that is shown in FIG. 7A. As illustrated in FIG. 7C, the prosthetic tissue valve, now denoted 10d, comprises a multi-layer or sheet (each sheet denoted "31") conical shaped member 30 having an annular ring 38 disposed between each sheet 31. According to the invention, the annular ring is designed and configured to securely engage the prosthetic tissue valve 10d to a valve annulus (and, hence, cardiovascular tissue associated therewith).

According to the invention, the outer circumference of the annular ring 38 can comprise various dimensions. In some embodiments of the invention, the ratio of the circumference of the annular ring 38 to the operative valve circumference of prosthetic tissue valve 10c (and prosthetic tissue valves 10d-10h) is in the range of approximately 1:1 to approximately 3:1.

Figure 7D:
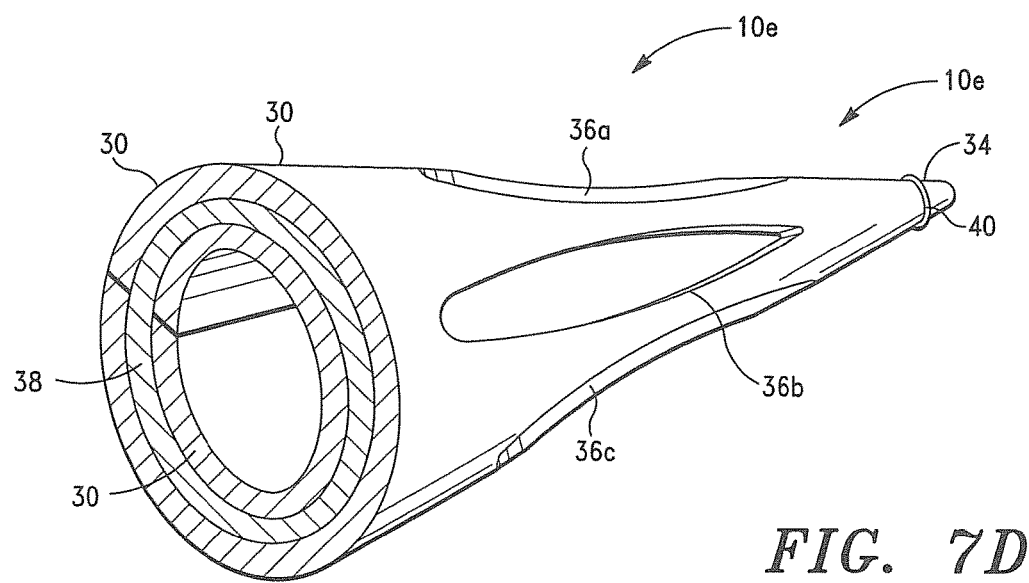
FIG. 7D is a perspective view partial sectional of yet another embodiment of a prosthetic tissue valve shown in FIG. 7A having an annular ring disposed at the proximal end of the valve and a structural ring disposed at the distal end of the valve, in accordance with the invention.

Referring now to FIG. 7D, there is shown yet another embodiment of the prosthetic tissue valve 10c that is shown in FIG. 7A. As illustrated in FIG. 7D, the prosthetic tissue valve, now denoted 10e, further comprises a structural ring 40 that is disposed on the distal end 34 of the valve 10e.

As indicated above, according to the invention, the annular ring 38 and/or structural ring 40 can comprise various biocompatible materials, such as disclosed in Co-Pending U.S. application Ser. No. 14/953,548.

In some embodiments of the invention, the annular ring 38 and/or structural ring 40 comprise a polymeric composition comprising one of the aforementioned biodegradable polymeric materials.

In some embodiments, the annular ring 38 and/or structural ring 40 comprise poly(urethane urea).

In some embodiments, the annular ring 38 and/or structural ring 40 comprise poly(glycerol sebacate) (PGS).

In some embodiments, the annular ring 38 and/or structural ring 40 comprise an ECM composition comprising acellular ECM derived from one of the aforementioned mammalian tissue sources.

Figure 8A:
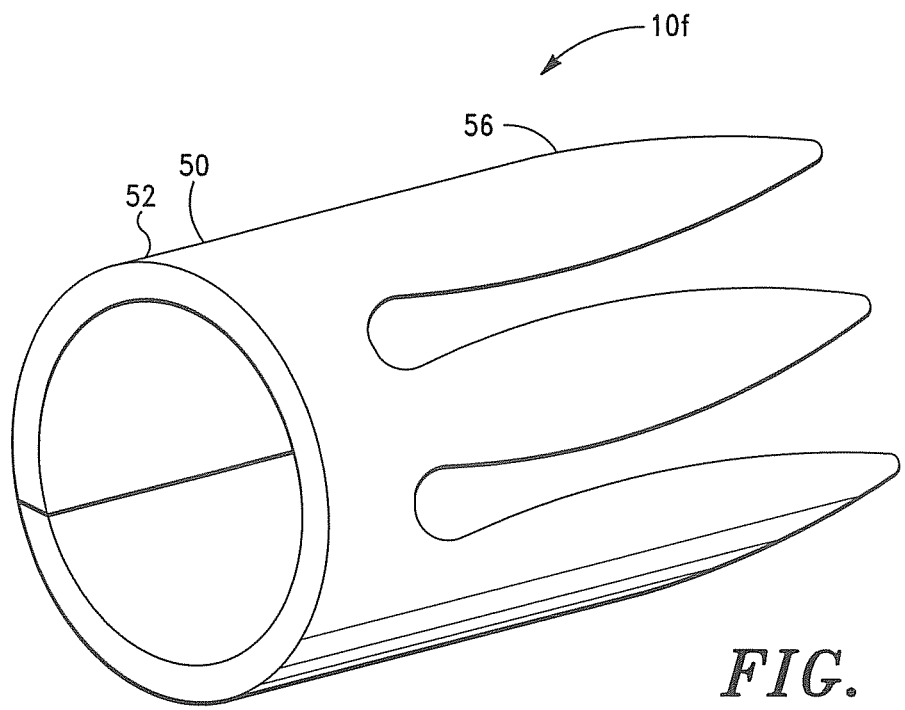
FIG. 8A is a side plan view of another embodiment of a prosthetic tissue valve in a pre-formed configuration, in accordance with the invention.
Figure 8B:
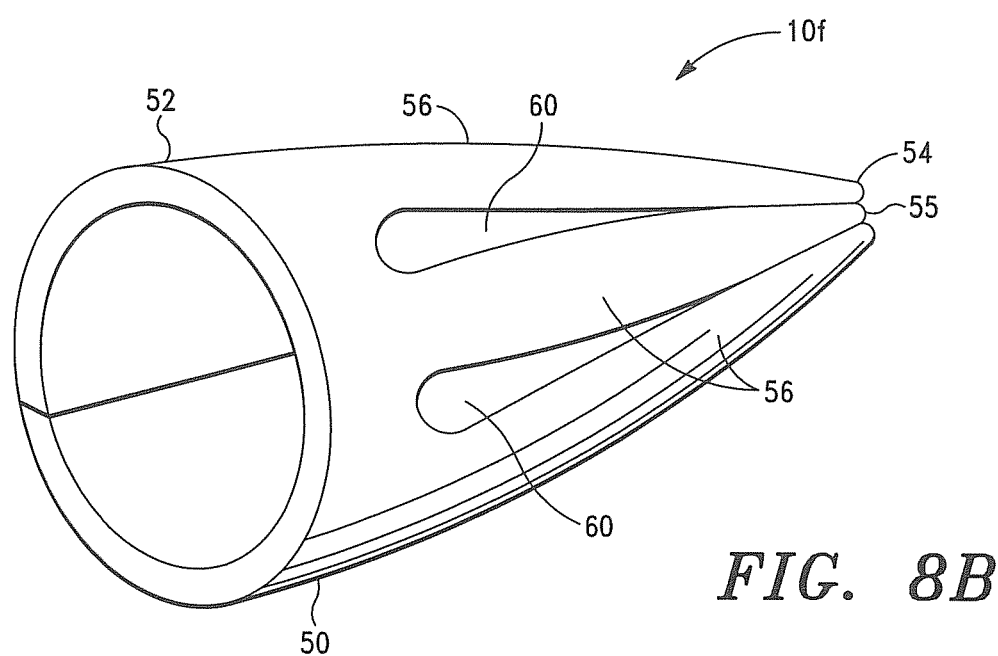
FIG. 8B is a perspective view of the prosthetic tissue valve shown in FIG. 8A in a formed configuration, in accordance with the invention.

Referring now to FIGS. 8A and 8B there is shown another embodiment of a prosthetic tissue valve of the invention, where FIG. 8A illustrates the prosthetic tissue valve, denoted 10f, in a pre-formed configuration and FIG. 8B illustrates the prosthetic tissue valve 10f in a formed configuration.

As illustrated in FIGS. 8A and 8B, in a preferred embodiment of the invention, the prosthetic tissue valve 10f comprises a base member 50 comprising a proximal valve annulus engagement end 52 and a distal end 54. The base member 50 further comprises a plurality of ribbons 56 that are connected to and extend from the proximal end 52 toward the distal end 54 of the base member 50.

As further illustrated in FIGS. 8A and 8B, each of the plurality of ribbons 56 comprise proximal and distal ends and opposing edge regions that extend from the proximal end to distal end of each of the ribbons 56 and, hence, distal end 54 of the base member 50.

In a preferred embodiment, the base member 50 similarly comprises an ECM composition comprising acellular ECM derived from one of the aforementioned mammalian tissue sources.

As illustrated in FIG. 8B, in some embodiments, the ribbons 56 of the formed valve 10f taper to a substantially coincident point 55, wherein the base member 50 has a substantially conical shape.

In a preferred embodiment of the invention, the distal ends of the ribbons 56 are engaged to each other in a joined relationship, wherein fluid flow through the distal end 54 of the base member 50 is restricted when the fluid modulating regions 60 (discussed below) are in open and closed positions.

As further illustrated in FIG. 8B, the ribbons 56 are positioned circumferentially about the base member 50, wherein the opposing edge regions of the ribbons 56 are positioned adjacent each other and form a plurality of fluid flow modulating regions 60.

In a preferred embodiment of the invention, the base member 50 and, hence, prosthetic tissue valve 10f (and valves 10g and 10h, discussed below) is similarly configured to transition from an expanded position, when the proximal end 52 of the base member 50 is engaged to a cardiovascular structure and receives fluid flow therein that exhibits a positive flow pressure, to a collapsed position when the fluid flow exhibits a negative flow pressure.

In a preferred embodiment, the fluid flow modulating regions 60 are configured to transition from an open position, i.e. the opposing edge regions are separated, when the proximal end 52 of the base member 50 is engaged to a cardiovascular structure and receives fluid flow therein that exhibits a positive flow pressure, and the base member 50 is in the expanded position, to a closed position when the fluid flow exhibits a negative fluid flow pressure and the base member 50 is in the collapsed position.

As indicated above, the distal end of the ribbons 56 are engaged or connected to each other in a joined relationship at the distal end 54 of the base member 50, wherein fluid flow through the distal end 54 of the base member 50 is restricted, whereby, when the proximal end 52 of the base member 50 is engaged to a cardiovascular structure, fluid flow exhibiting a positive flow pressure is introduced into the proximal end 52 of the base member 50 and the base member 30 is in an expanded position, and the plurality of fluid flow modulating regions 60 are in the open position, the plurality of fluid flow modulating regions 60 allow the fluid flow to be transmitted through the plurality of open flow modulating regions and, hence, base member 50, and when the fluid flow exhibits a negative flow pressure and the base member 50 is in the collapsed position, and the plurality of fluid flow modulating regions 60 are in the closed position, the plurality of closed fluid flow modulating regions 60 and joined distal ends of the ribbons 56 restrict fluid flow through the base member 50.

According to the invention, the base member 50 can comprise any number of ribbons 56. In some embodiments of the invention, the base member 50 has four (4) equally spaced ribbons 56.

According to the invention, the proximal end 52 of the valve 10f is similarly sized and configured to engage an annular region of a mammalian heart.

According to the invention, the proximal end 52 of the valve 10f (and prosthetic tissue valves 10g and 10h, discussed below) can similarly comprise a circumference, i.e. operative valve circumference, in the range of approximately 20 mm to 220 mm.

According to the invention, the prosthetic tissue valve 10f (and prosthetic tissue valves 10g and 10h, discussed below) can also comprise any length. In some embodiments of the invention, the prosthetic tissue valve 10f (and prosthetic tissue valves 10g and 10h) has a length in the range of approximately 5 mm to 150 mm. In some embodiments of the invention, the prosthetic tissue valve 10f (and prosthetic tissue valves 10g and 10h) has a length in the range of approximately 10 mm to 100 mm.

In some embodiments of the invention, prosthetic tissue valve 10f (and valves 10g and 10h) has a proximal end diameter and length ratio in the range of 5:1 to 2:1.

Figure 8C:
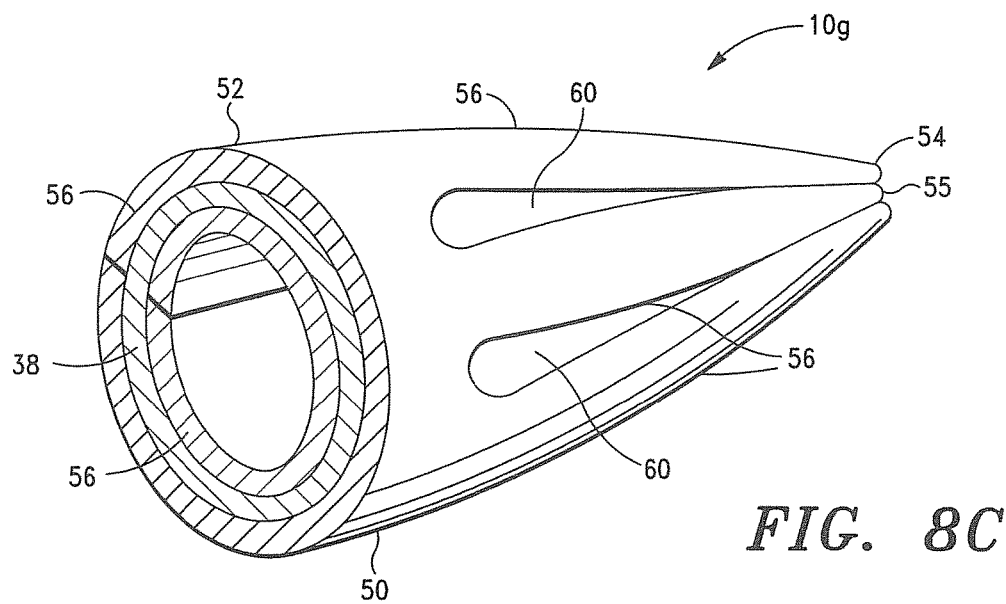
FIG. 8C is a perspective partial sectional view of another embodiment of a prosthetic tissue valve shown in FIG. 8B having an annular ring disposed at the proximal end of the valve, in accordance with the invention.

Referring now to FIG. 8C, there is shown another embodiment of the prosthetic tissue valve 10f that is shown in FIG. 8B. As illustrated in FIG. 8C, the prosthetic tissue valve, now denoted 10g, comprises a multi-layer or sheet (each sheet denoted "57") base member 50 having an annular ring 38 disposed between each sheet 57, which is similarly designed and configured to securely engage the prosthetic tissue valve 10g to a valve annulus (and, hence, cardiovascular tissue associated therewith).

Figure 8D:
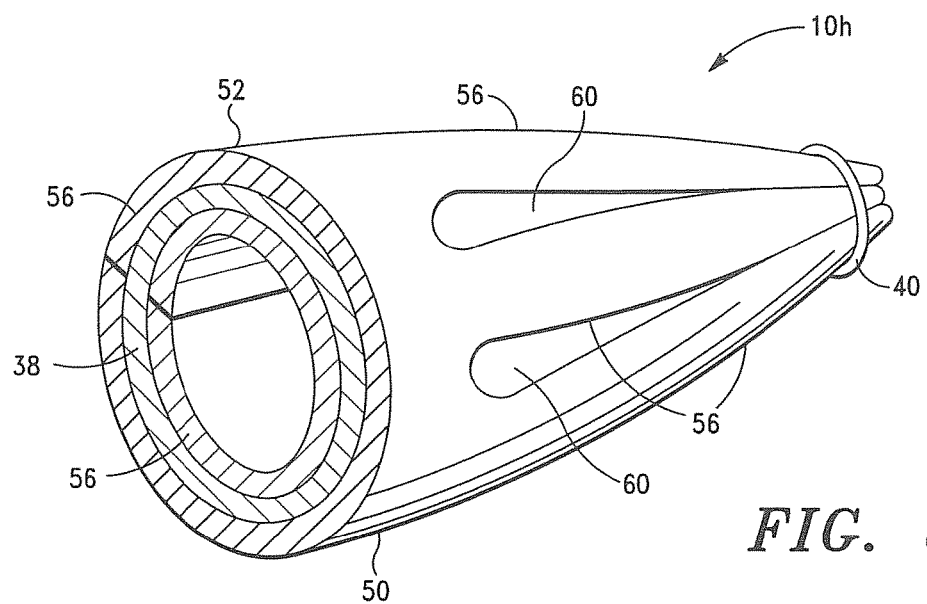
FIG. 8D is a perspective partial sectional view of yet another embodiment of a prosthetic tissue valve shown in FIG. 8B having an annular ring disposed at the proximal end of the valve and a structural ring disposed at the distal end of the valve, in accordance with the invention.

Referring now to FIG. 8D, there is shown yet another aspect of the prosthetic tissue valve 10f that is shown in FIG. 8B. As illustrated in FIG. 8D, the prosthetic tissue valve, now denoted 10h, further comprises a structural ring 40 that is disposed on the distal end 54 of the valve 10h.

According to the invention, the structural ring 40 is preferably sized and configured to receive ribbons 56 therein in close proximity to each other, as shown in FIG. 8D.

According to the invention, the proximal end of the prosthetic tissue valves of the invention can be secured to a valve annulus by various conventional means, such as suturing the proximal end (with or without an annular ring 38) directly to the valve annulus tissue.

In some embodiments of the invention, ribbons 56 of prosthetic valves 10f, 10g and 10h are connected via a constraining band that is positioned between the proximal and distal ends 52, 54 of the valves 10f, 10g, 10h. According to the invention, the restraining band can comprise the same material as the valve base member 50 or a different material.

In some embodiments of the invention, ribbons 56 of prosthetic valves 10f, 10g and 10h are restrained at a predetermined valve region, e.g., mid-point, between the proximal and distal ends 52, 54 of the valves 10f, 10g, 10h via a supplemental structural ring.

As indicated above, in a preferred embodiment of the invention, the conical shaped member 30 of prosthetic tissue valves 10c-10d and base member 50 (and, hence, ribbons 56) of prosthetic tissue valves 10f-10h comprise an ECM composition comprising acellular ECM derived from one of the aforementioned mammalian tissue sources.

In some embodiments of the invention, the mammalian tissue source comprises small intestine submucosa (SIS).

In some embodiments, the mammalian tissue source comprises mesothelial tissue.

In some embodiments of the invention, the ECM composition and, hence, conical shaped member 30 of prosthetic tissue valves 10c-10d and base member 50 (and, hence, ribbons 56) of prosthetic tissue valves 10f-10h, further comprises at least one additional biologically active agent or composition, i.e. an agent that induces or modulates a physiological or biological process, or cellular activity.

In some embodiment, the annular ring 38 and/or structural ring 40 comprise at least one additional biologically active agent or composition.

According to the invention, suitable biologically active agents include any of the aforementioned biologically active agents.

In some embodiments of the invention, the ECM composition and, hence, conical shaped member 30 of prosthetic tissue valves 10c-10d and base member 50 (and, hence, ribbons 56) of prosthetic tissue valves 10f-10h, further comprises at least one pharmacological agent or composition (or drug), i.e. an agent or composition that is capable of producing a desired biological effect in vivo.

In some embodiment, the annular ring 38 and/or structural ring 40 comprise at least one additional pharmacological agent or composition.

According to the invention, suitable pharmacological agents and compositions include any of the aforementioned agents, including, without limitation, antibiotics, and anti-inflammatories.

In some embodiments of the invention, the conical shaped member 30 of prosthetic tissue valves 10c-10d and base member 50 (and, hence, ribbons 56) of prosthetic tissue valves 10f-10h comprise an outer coating.

In some embodiments, the annular ring 38 and/or structural ring 40 comprise an outer coating.

In some embodiments of the invention, the coating comprises an ECM composition comprising acellular ECM form one of the aforementioned mammalian tissue sources.

In some embodiments, the ECM composition further comprises at least one of the aforementioned biologically active agents or compositions.

In some embodiments, the ECM composition further comprises at least one of the aforementioned pharmacological agents or compositions.

In some embodiments of the invention, the coating comprises one of the aforementioned polymeric compositions.

Referring now to FIG. 9, placement of prosthetic tissue valve 10d in a mitral valve region will now be described in detail.

According to the invention, prior to placement of prosthetic tissue vale 10d (as well as valves 10c and 10e-10h) in a mitral valve region, the mitral valve 102 and chordae tendinae 103a, 103b can be removed or retained. Thus, in some embodiments of the invention, the mitral valve 102 and chordae tendinae 103a, 103b are retained. In some embodiments, the mitral valve 102 and chordae tendinae 103a, 103b are removed.

After the mitral valve annulus region 107 is prepared, and, if elected, the mitral valve 102 and chordae tendinae 103a, 103b are removed, the prosthetic tissue valve 10d is disposed proximate the mitral valve annulus region 107.

According to the invention, the initial placement of the prosthetic tissue valve 10d (as well as tissue valves 10a-10c and 10e-10h, discussed below) can be achieved by various conventional means, including limited access heart surgery and percutaneous transatrial, i.e. through the left atrium, and transapical delivery.

After disposing the prosthetic tissue valve 10d proximate the mitral valve region 107, the proximal end 32 of the prosthetic tissue valve 10d is secured to the valve annulus 105.

Figure 10:
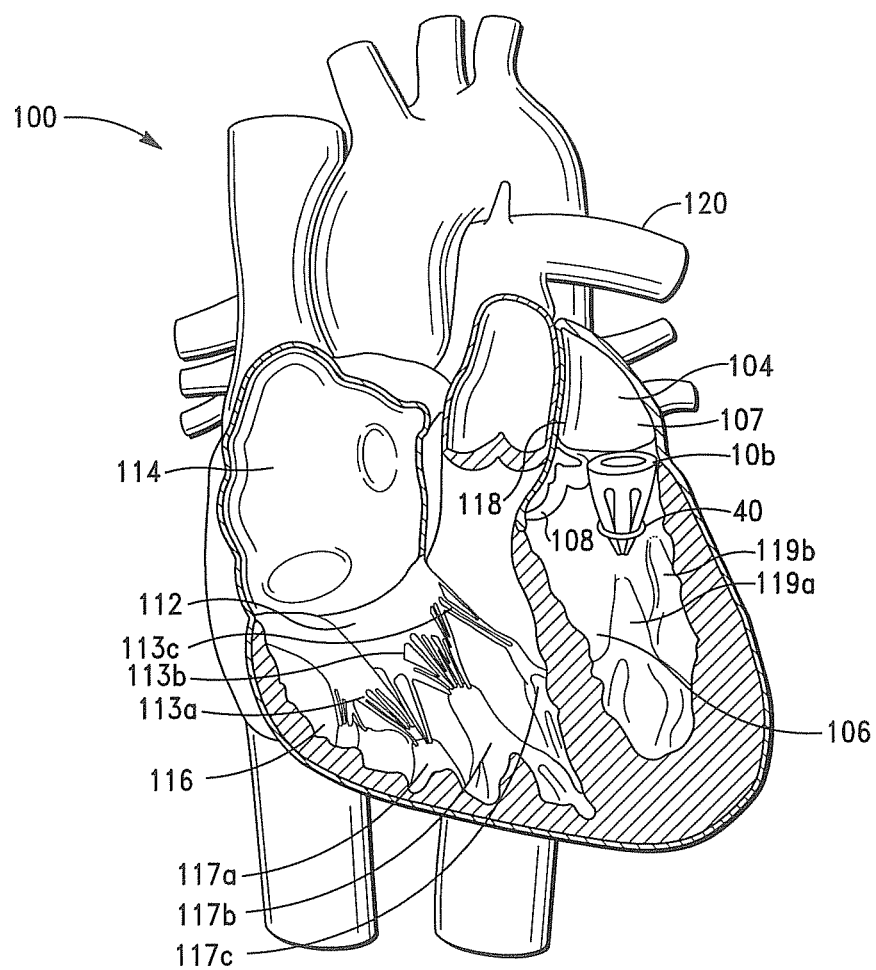
FIG. 10 is an illustration of the prosthetic tissue valve shown in FIG. 8C secured to the mitral valve annulus region, in accordance with the invention.

Referring now to FIG. 10, placement of prosthetic tissue valve 10h in a mitral valve region will now be described in detail.

After the mitral valve annulus region 107 is prepared and, if elected, the mitral valve 102 and chordae tendinae 103a, 103b are removed, the valve 10h is similarly disposed proximate the mitral valve annulus region 107. The proximal end 32 of the prosthetic tissue valve 10h is then secured to the valve annulus 105.

Placement of prosthetic tissue valves 10f and 10g in a mitral valve region are similar to placement of prosthetic tissue valve 10h. However, in some embodiments of the invention, the distal ends 54 of the ribbons 56 proximate the coincident point 55 of prosthetic tissue valves 10f and 10g are connected to the inner surface of the ventricle 106 via at least one active fixation lead (not shown).

Figure 11:
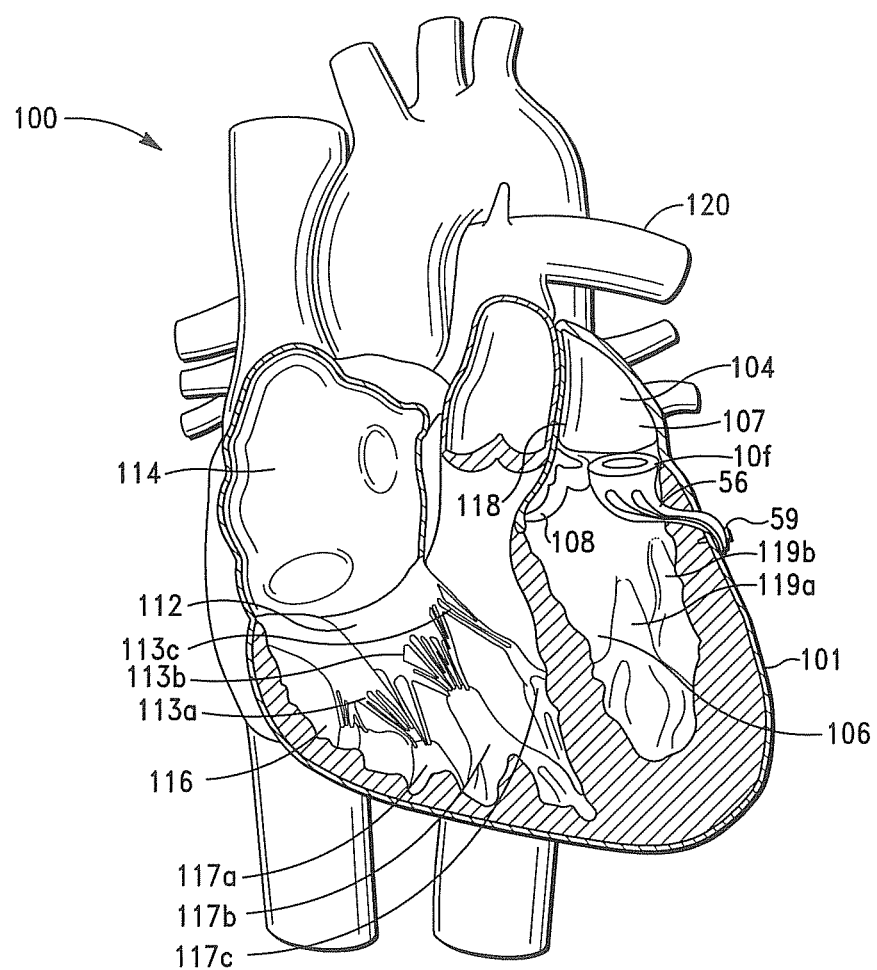
FIG. 11 is an illustration of the prosthetic tissue valve shown in FIG. 8B secured to the mitral valve annulus region, in accordance with the invention.

As illustrated in FIG. 11, in some embodiments of the invention, the ribbons 56 are threaded through the heart wall 101 and attached on the outside of the heart 100 in a joined relationship, wherein fluid flow through the base member 50 at the distal end 54 of the valve 10f is restricted. In some embodiments, the ribbons 56 are secured into the heart wall muscle via cork-screw mechanism 59.

In some embodiments of the invention, the prosthetic tissue valves 10c-10h described above further comprise a supplemental support structure. In some embodiments, the support structure comprises at least one internal biocompatible support ring that is disposed between the proximal and distal end of the valve. In some embodiments, the support structure comprises a biocompatible multi-link stent structure.

In some embodiments of the invention, the prosthetic tissue valves 10c-10h described above further comprise at least one internal pre-formed leaflet, such as disclosed in Applicant's U.S. Pat. Nos. 8,709,076, 9,011,526, 8,257,434 and 7,998,196, which are incorporated by reference herein.

As indicated above, it is contemplated that, when the prosthetic tissue valves 10c-10h comprise an ECM composition comprising acellular ECM (i.e. ECM prosthetic tissue valves), upon placement of the ECM prosthetic tissue valves 10c-10h to a valve structure, e.g., valve annulus 105, modulated healing of the valve structure and connecting cardiovascular structure tissue will be effectuated.

It is further contemplated that, following placement of the ECM prosthetic tissue valves 10c-10h in a subject on a cardiovascular structure (or structures) in a subject, the ECM prosthetic tissue valves 10c-10h will become populated with cells from the subject that will gradually remodel the ECM into cardiovascular tissue and tissue (and, hence, valve) structures.

It is further contemplated that, following placement of the ECM prosthetic tissue valves 10c-10h in a subject on a cardiovascular structure (or structures) in a subject, stem cells will migrate to the ECM prosthetic tissue valves 10c-10h from the point(s) at which the valves are attached to the cardiovascular structure, e.g., valve annulus, or structures, e.g., valve annulus and heart wall.

It is still further contemplated that the points at which the ECM prosthetic tissue valves 10c-10h are attached to a cardiovascular structure (or structures) in a subject will serve as points of constraint that direct the remodeling of the ECM into cardiovascular tissue and valve structures that are identical or substantially identical to properly functioning native cardiovascular tissue and valve structures.

It is still further contemplated that, during circulation of epithelial and endothelial progenitor cells after placement of the ECM prosthetic tissue valves 10c-10h on a cardiovascular structure (or structures), the surfaces of an ECM prosthetic tissue valves 10c-10h will rapidly become lined or covered with epithelial and/or endothelial progenitor cells.

As will readily be appreciated by one having ordinary skill in the art, the present invention provides numerous advantages compared to prior art prosthetic valves. Among the advantages are the following:

The provision of improved methods for securely attaching prosthetic valves to cardiovascular structures and/or tissue;

The provision of prosthetic tissue valves having means for secure, reliable, and consistently highly effective attachment to cardiovascular structures and/or tissue;

The provision of improved prosthetic tissue valves and methods for attaching same to cardiovascular structures and/or tissue that maintain or enhance the structural integrity of the valve when subjected to cardiac cycle induced stress;

The provision of improved prosthetic tissue valves and methods for attaching same to cardiovascular structures and/or tissue that preserve the structural integrity of the cardiovascular structure(s) when attached thereto;

The provision of prosthetic tissue valves that induce modulated healing, including host tissue proliferation, bioremodeling and regeneration of new tissue and tissue structures with site-specific structural and functional properties;

The provision of prosthetic tissue valves that induce adaptive regeneration;

The provision of prosthetic tissue valves that are capable of administering a pharmacological agent to host tissue and, thereby produce a desired biological and/or therapeutic effect;

The provision prosthetic tissue valves that can be implanted without removal of the native AV valve;

The provision prosthetic tissue valves that can be implanted without a cardiopulmonary bypass apparatus;

The provision prosthetic tissue valves that can be positioned proximate a valve annulus transvascularly; and The provision prosthetic tissue valves that can be positioned proximate a valve annulus transapically.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A prosthetic valve for modulating fluid flow through a cardiovascular structure during cardiac cycles of a heart, said fluid flow exhibiting a plurality of positive and negative flow pressures during said cardiac cycles, said prosthetic valve comprising:

a remodelable biological tissue structure comprising a continuous tubular member, said tubular member comprising an adaptive tissue regeneration system configured to engage said cardiovascular structure and induce modulated healing of damaged cardiovascular tissue of said cardiovascular structure concomitantly with stress-induced hypertrophy of said tubular member when said tubular member is subjected to cardiac cycle induced physical stimuli, said modulated healing of said damaged cardiovascular tissue comprising inflammation modulation of said damaged cardiovascular tissue and induced neovascularization, remodeling of said damaged cardiovascular tissue and regeneration of new cardiovascular tissue and tissue structures with site-specific structural and functional properties, said stress-induced hypertrophy of said tubular member comprising adaptive remodeling of said tubular member, wherein said tubular member remodels and forms functioning valve structures that are similar to native valve structures, said adaptive tissue regeneration system comprising a tubular member material component and a tubular member physical structure component, said tubular member material component comprising an extracellular matrix (ECM) composition, said ECM composition comprising acellular ECM from a mammalian tissue source, said tubular member physical structure component comprising a sheet member comprising a proximal valve annulus engagement end and a distal end, said proximal valve annulus engagement end of said sheet member being configured to engage a valve annulus region of said cardiovascular structure, said proximal valve annulus engagement end comprising a circumferential ribbon connection region and a plurality of equally spaced ribbons projecting from said circumferential ribbon connection region toward said sheet member distal end, each of said plurality of ribbons comprising proximal and distal ends, a first edge region extending from said proximal end of each of said plurality of ribbons to said distal end of each of said plurality of ribbons and a second edge region extending from said proximal end of each of said plurality of ribbons to said distal end of each of said plurality of ribbons, said proximal end of each of said plurality of ribbons being connected to said circumferential ribbon connection region, said plurality of ribbons being positioned circumferentially about said circumferential ribbon connection region, wherein said first edge regions of said plurality of ribbons are positioned proximate said second edge regions of said plurality of ribbons, wherein a plurality of fluid flow modulating regions is formed between adjacent ribbons of said plurality of ribbons, said distal ends of said plurality of ribbons being engaged to each other in a joined relationship, wherein fluid flow through said sheet member at said joined distal ends of said plurality of ribbons is restricted while said fluid flow is allowed to be transmitted through said fluid flow modulating regions when in an open position, said sheet member being configured to transition from an expanded position when said proximal valve annulus engagement end of said sheet member is engaged to said valve annulus region of said cardiovascular structure and receives said fluid flow therein, and said fluid flow exhibits a first positive flow pressure of said plurality of positive flow pressures, to a collapsed position when said fluid flow exhibits a first negative flow pressure of said plurality of negative flow pressures, said plurality of fluid flow modulating regions being configured to transition from said open position when said sheet member is in said expanded position, wherein said plurality of fluid flow modulating regions allow said fluid flow to be transmitted through said sheet member, to a closed position when said sheet member is in said collapsed position, wherein said plurality of fluid flow modulating regions restrict said fluid flow through said sheet member.

2. The prosthetic valve of claim 1, wherein said mammalian tissue source is selected from the group consisting of small intestine submucosa (SIS), urinary bladder submucosa (UBS), urinary basement membrane (UBM), liver basement membrane (LBM), stomach submucosa (SS), mesothelial tissue, placental tissue, and cardiac tissue.

3. The prosthetic valve of claim 1, wherein said ECM composition further comprises at least one exogenously added biologically active agent.

4. The prosthetic valve of claim 3, wherein said biologically active agent comprises a cell selected from the group consisting of a human embryonic stem cell, fetal cardiomyocyte, myofibroblast, and mesenchymal stem cell.

5. The prosthetic valve of claim 3, wherein said biologically active agent comprises a growth factor selected from the group consisting of a transforming growth factor-alpha (TGF-α), transforming growth factor-beta (TGF-β), fibroblast growth factor-2 (FGF-2), and vascular epithelial growth factor (VEGF).

6. The prosthetic valve of claim 1, wherein said ECM composition further comprises a pharmacological agent.

7. The prosthetic valve of claim 6, wherein said pharmacological agent comprises an agent selected from the group consisting of an antibiotic, anti-viral agent, analgesic, anti-inflammatory, anti-neoplastic, anti-spasmodic, and anticoagulant and antithrombotic agent.

8. The prosthetic valve of claim 6, wherein said pharmacological agent comprises a statin selected from the group consisting of atorvastatin, cerivastatin, fluvastatin, lovastatin, mevastatin, pitavastatin, pravastatin, rosuvastatin and simvastatin.

9. The prosthetic valve of claim 1, wherein said sheet member further comprises an outer coating comprising a pharmacological composition.

* * * * *